US006121427A

United States Patent [19]
Yang et al.

[11] Patent Number: 6,121,427
[45] Date of Patent: Sep. 19, 2000

[54] MAJOR OUTER MEMBRANE PROTEIN CD OF BRANHAMELLA

[75] Inventors: Yan-Ping Yang; Robin Edmond Harkness, both of Willowdale; Lisa Elizabeth Myers, Guelph; Ursula McGuiness, Richmond Hill; Michel Henri Klein, Willowdale, all of Canada

[73] Assignee: Connaught Laboratories Limited, North York, Canada

[21] Appl. No.: 08/474,394

[22] Filed: Jun. 7, 1995

Related U.S. Application Data

[63] Continuation of application No. 08/328,589, Oct. 24, 1994, abandoned.

[51] Int. Cl.[7] .............................. A23J 1/00; C07K 14/00; A61K 39/00; A61K 39/095
[52] U.S. Cl. .......................... 530/412; 530/413; 530/414; 424/184.1; 424/251.1
[58] Field of Search .............................. 424/251.1, 184.1; 530/412, 414, 413

[56] References Cited

U.S. PATENT DOCUMENTS

| | | |
|---|---|---|
| 5,010,000 | 4/1991 | Palva . |
| 5,075,223 | 12/1991 | Lubitz et al. . |
| 5,110,908 | 5/1992 | Deich et al. . |
| 5,141,743 | 8/1992 | Schryvers . |
| 5,292,869 | 3/1994 | Schryvers . |
| 5,393,658 | 2/1995 | Olsen . |
| 5,552,146 | 9/1996 | Hansen et al. . |
| 5,556,755 | 9/1996 | Murphy . |

FOREIGN PATENT DOCUMENTS

| | | |
|---|---|---|
| 0624376 | 5/1994 | European Pat. Off. . |
| 90/13032 | 11/1990 | WIPO . |

OTHER PUBLICATIONS

Zlatnick et al, JBC, 263/20:9790–9794, Jul. 1988.
James et al J. Immunal. Methods 42:223–228, 1981.
Schnaitman, J. Bacteriol, 108/1:553–563, Oct. 1971.
Mandrell et al., J. Immunol. Methods 67:1–11, 1984.
Wedege et al, J. Immunol. Methods 113:51–59, 1988.
Collins et al, Infect. & Immun. 30/1:281–288, Oct., 1980.
Smyth. In:Immunology of the Bacterial Cell Envelope Editor Stewirt–Tull et al pp. 177–201, 1985.
Murphy et al, 1989, Microbial Pathogenesis 6:159–174.
Murphy et al 1990 Am J. Med. 88(Suppl 5A):5A–41S–5A–45S.
Sethi et al, 1995 Infec & Imm. 63(4):1516–1520.
Hsiao et al, 1995. Microbial Pathogenesis 19:215–225.
Van Hare, G.F., P.A. Shurin, C.D. Marchant, N.A. Cartell, C.E. Johnson, D. Fulton, S. Carlin, and C.H. Kim. Acute otitis media caused by *Branhamella catarrhalis*: biology and therapy. Rev. Infect. Dis. 9:16–27.
Chapman, A.J., D.M. Musher, S. Jonsson, J.E. Claridge, and R.J. Wallace. 1985. Development of bactericidal antibody during *Branhamella catarrhalis* infection. J. Infect. Dis. 151:878–882.

Hager, H., A. Verghese, S. Alvarez, and S.L. Berk. 1987. *Branhaella catarrhalis* respiratory infections. Rev. Infect. Dis. 9:1140–149.
McLeod, D.T., F. Ahmad, M.J. Croughan, and M.A. Calder, 1986. Bronchopulmonary infection due to *B. catarhalis*. Clinical features and therapeutic response. Drugs 31(Suppl.3):109–112.
Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.
Ninane, G., J. Joly, and M. Krytman. 1978. Bronchopulmonary Infection due to *Branhamella catarrhalis* 11 cases assesed by transtracheal puncture. Br.Med.Jr. 1:276–278.
Srinivasan, G., M.J. Raff, W.C. Templeton, S.J. Givens, R.C. Graves, and J.C. Mel. 1981. *Branhamella catarrhalis* pneumonia. Report of two cases and review of the literature. Am.Rev. Respir. Dis. 123:553–555.
West, M., S.L. Berk, and J.K. Smith. 1982. *Branhamella catarrhalis* pneumonia. South.Med. J. 75:1021–1023.
Boroson, J–E., A. Axelsson, and S.E. Holm. 1976. Studies on *Branhamella catarrhalis* (*Neisseria catarrhalis*) with special reference to maxillary sinusitis. Scan. J. Infect. Dis 8:151–155.
Evans, F.O., Jr. J.B. Sydnor, W.E.C. Moore, G.R. Moore, J.L. Manwaring, A.H. Brill, R.T. Jackson, S. Hanna, J.S. Skaar, L.V. Holdeman, G.S. Fitz–hugh, M.A. Sande, and J.M. Gwaltney, Jr. 1975. Sinusitis of the maxillary antrum. N.Engl.J.Med. 293:735–739.
Tinkleman, D.G., and H.J. Silk. 1989. Clinical and bacterioloogic features of chronic sinusitis in children. Am.J.Dis.Child. 143:938–942.
Wald, E.R., C. Byers, N.Guerra, M.Casselbrant, and D. Beste. 1989. Subacute sinusitis in children. J.Pediatr. 115:28–32.

(List continued on next page.)

*Primary Examiner*—Nita Minnifield
*Attorney, Agent, or Firm*—Sim & McBurney

[57] ABSTRACT

An isolated and purified non-denatured outer membrane protein CD which is that of or corresponds to that isolatable from a Branhamella strain, particularly *B. catarhalis*, is isolated from a bacterial strain by fractionating a cell lysate formed by disrupting a cell mass of the bacterial strain by centrifugation to provide a pellet and a discard supernatant containing a large proportion of soluble bacterial proteins. The pellet is selectively extracted to remove the remaining soluble proteins, the membrane proteins other than CD and other contaminants such as lipopolysaccharide and phospholipids. The remaining CD-containing pellet is dispersed and solubilized and then fractionated by centrifugation to remove the remaining cell debris. The CD protein is useful in diagnostic applications and immunogenic compositions, particularly for in vivo administration to a host to confer protection against disease caused by a bacterial pathogen that produces CD protein or produces a protein capable of inducing antibodies in a host specifically reactive with CD protein.

10 Claims, 7 Drawing Sheets

OTHER PUBLICATIONS

Wald, E.R., G.J. Milmoe, A. Bowen, J.Ledesma–Medina, N. Salamon, and C.D.Bluestone. 1981. Acute maxillary sinusitis in children, N.Engl.J.Med. 304:749–754.

Christensen, J.J., and B. Bruun. 1985. Bacteremia caused by a beta–lactamase producing strain of *Branhamella catarrhalis.* Acta.Pathol. Microbiol. Immunol. Scand. Sect. B 93:273–275.

Craig, D.B., and P.A. Wehrle. 1983. *Branhamella catarrhalis* septic arthrits. J. Rheumatol. 10:985–986.

Gray, L.D., R.E. Van Scoy, J.P. Anhalt, and P.K.W. Yu. 1989. Wound infection caused by *Branhamella catarrhalis.* J.Clin, Microbiol. 27:818–820.

Guthrie, R., K. Bakenhaster, R.Nelson, and R.Woskobnick. 1988. *Branhamella catarrhalis* sepsis: a case report and review of the literature. j.Infect.Dis. 158:907–908.

Hiroshi, S., Anaisse, N.Khardori, and G.P. Bodey. 1988. *Branhamella catarrhalis* septicemia in patients with leukemia. Cancer 61:2315–2317.

O'Neill, J.H., and P.W. Mathieson. 1987. Meningitis due to *Branhamella catarrhalis.* Aust. N.Z. J. Med. 17:241–242.

Murphy, T.F. 1989. The Surface of *Branhamella catarrhalis:* A Systematic Approach to the Surface Antigens of an Emerging Pathogen. Pediatr. Infect. Dis. J. 8:S75–S77.

Sarwar, J. Campagnari, A.A., Kirkham, C., and Murphy, T.F. 1992, Charcterization of an antigen conserved heat–modifiable major outer membrane protein of *Branhamella catarrhalis.* 1992. Infect.Immun. 60:804–809.

Murphy, T.F., C. Kirkham, and A.J. Lesse. 1993. The major heat–modifiable outer membrane protein CD is highly conserved among strains of *Branhamella catarrhalis.* Mol. Microbiol. 10(1):87–97.

Panezutti H., O. James, E.J. Hanson, Y. Choi, R.E. Harkness, M.H. Klein and P. Chong, 1993. Identification of surface–exposed B–cell epitopes recognized by *Haemophilus influezae* type b P1 specific monoclonal antibodies. Infec. Immun. 61: 1867–1872.

Nixon–George et al. (1990), J. Immunology 144:4798–4802.

Wiesmuller (1989), Vaccine 8:29–33.

Deres et al. (1989), Nature 342:561.

Lockhoff, O. Glycolipids as Immunomodulators: Synthesis and Properties. 1991. Chem. Int. Ed. Engl. 30:1611–1620.

MAJOR OUTER MEMBRANE PROTEIN CD OF BRANHAMELLA

This is a continuation of application Ser. No. 08/328,589 filed Oct. 24, 1994 now abandoned.

FIELD OF THE INVENTION

The present invention relates to the field of immunology and is particularly concerned with major outer membrane proteins from Branhamella, methods of production thereof and uses thereof.

BACKGROUND OF THE INVENTION

Otitis media is the most common illness of early childhood with approximately 70% of all children suffering at least one bout of otitis media before the age of seven. Chronic otitis media can lead to hearing, speech and cognitive impairment in children. It is caused by bacterial infection with *Streptococcus pneumoniae* (approximately 50%), non-typable *Haemophilus influenzae* (approximately 30%) and *Moraxella* (Branhamella) *catarrhalis* (approximately 20%). In the United States alone, treatment of otitis media costs between one and two billion dollars per year for antibiotics and surgical procedures, such as tonsillectomies, adenoidectomies and insertion of tympanostomy tubes. Because otitis media occurs at a time in life when language skills are developing at a rapid pace, developmental disabilities specifically related to learning and auditory perception have been documented in youngsters with frequent otitis media.

*B. catarrhalis* mainly colonizes the respiratory tract and is predominantly a mucosal pathogen. Studies using cultures of middle ear fluid obtained by tympanocentesis have shown that *B. catarrhalis* causes approximately 20% of cases of otitis media. (ref. 1–Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure.)

The incidence of otitis media caused by *B. catarrhalis* is increasing. As ways of preventing otitis media caused by pneumococcus and nontypeable *H. influenzae* are developed, the relative importance of *B. catarrhalis* as a cause of otitis media can be expected to further increase.

*B. catarrhalis* is also an important cause of lower respiratory tract infections in adults, particularly in the setting of chronic bronchitis and emphysema (refs. 2, 3, 4, 5, 6, 7, and 8). *B. catarrhalis* also causes sinusitis in children and adults (refs. 9, 10. 11, 12, and 13) and occasionally causes invasive disease (refs. 14, 15, 16, 17, 18, and 19).

Like other Gram-negative bacteria, the outer membrane of *B. catarrhalis* consists of phospholipids, lipopolysaccharide (LPS), and outer membrane proteins (OMPs). Eight of the *B. catarrhalis* OMPs have been identified as major components. These are designated by letters A through H, beginning with OMP A which has a molecular mass of 98 kDa to OMP H which has a molecular mass of 21 kDa (ref. 20).

Of the major OMPs identified in *B. catarrhalis* an apparent doublet, named CD, is a heat modifiable protein. It has a molecular mass of 55 kDa at room temperature and a mass of 60 kDa when heated under reducing conditions. This protein is surface exposed and conserved among a variety of *B. catarrhalis* strains, as demonstrated by a study using CD-specific monoclonal antibodies (ref. 21). The gene encoding CD was recently cloned and expressed in *E. coli* by Murphy et al (ref. 22). Restriction mapping of 30 isolates of *B. catarrhalis* with oligonucleotide probes corresponding to sequences in the CD gene produced identical patterns in Southern blot assays, indicating the sequence of the CD gene to be highly conserved.

Thus, the heat-modifiable protein CD of *B. catarrhalis* is a surface exposed, conserved protein that contains at least two epitopes that are present in all studied strains of *B. catarrhalis* (ref. 21). Properties of CD protein indicate that the protein has utility in diagnosis of and vaccination against disease caused by *B. catarrhalis* or other bacterial pathogens that produce CD protein or produce a protein capable of raising antibodies specifically reactive with CD protein.

It would be advantageous to provide purified CD protein (and methods of purification thereof) for use as antigens, immunogenic preparations including vaccines, carriers for other antigens and immunogens and the generation of diagnostic reagents.

SUMMARY OF THE INVENTION

The present invention is directed towards the provision of purified major outer membrane protein CD of *Branhamella catarrhalis* and methods of purification of the CD protein.

In accordance with one embodiment of the invention, there is provided an isolated and purified, non-denatured outer membrane protein CD isolatable from a Branhamella strain. The CD protein may be substantially in its native conformation (so as to have substantially the characteristic immunogenicity of the CD protein in the Branhamella strain) and may be isolated from a *B. catarrhalis* strain, such as from *B. catarrhalis* 4223 or RH408. Such isolated and purified CD protein is substantially free from non-CD outer membrane protein, phospholipids and lipopolysaccharide of Branhamella.

The present invention also provides an immunogenic composition comprising an immunoeffective amount of the outer membrane protein as provided herein. The immunogenic composition may be formulated as a vaccine for in vivo administration to a host to confer protection against diseases caused by a bacterial pathogen that produces CD protein or produces a protein capable of inducing antibodies in the host specifically reactive with CD protein. In particular, the bacterial pathogen is *B. catarrhalis*. The immunogenic compositions of the invention (including vaccines) may further comprise at least one other immunogenic or immunostimulating material and the immunostimulating material may be at least one adjuvant. Suitable adjuvants for use in the present invention include, (but are not limited to) aluminum phosphate, aluminum hydroxide, QS21, calcium phosphate, calcium hydroxide, zinc hydroxide, a glycolipid analog, and octadecyl ester of an amino acid and a lipoprotein. Advantageous combinations of adjuvants are described in copending U.S. patent application Ser. No. 261,194 filed Jun. 16, 1994, assigned to the assignee hereof and the disclosure of which is incorporated herein by reference.

In a further aspect of the invention, there is provided a method of generating an immune response in a host comprising administering thereto an immuno-effective amount of the immunogenic composition as provided herein. The immune response may be a humoral or a cell-mediated immune response. The immune response may provide protection to the host against diseases caused by a bacterial pathogen that produces CD protein or produces a protein capable of inducing antibodies in the host specifically reactive with CD protein. Hosts in which protection against disease may be conferred include primates including humans.

In a further aspect of the invention, there is provided an antibody specific for the CD outer membrane protein and producible by immunizing a host with the immunogenic composition as provided herein.

In yet a further embodiment of the invention, there is provided a method of determining the presence of antibodies specifically reactive with outer membrane protein CD of *Branhamella catarrhalis* protein in a sample, comprising the steps of:

(a) contacting the sample with the CD protein as provided herein to produce complexes comprising the CD protein and any said antibodies present in the sample specifically reactive therewith; and (b) determining production of the complexes.

In a further aspect of the invention, there is also provided a method of determining the presence of CD protein in a sample comprising the steps of:

(a) immunizing a subject with the immunogenic composition as provided herein, to produce antibodies specific for CD protein;

(b) contacting the sample with the antibodies to produce complexes comprising any CD protein present in the sample and said CD protein specific antibodies; and (c) determining production of the complexes.

The CD protein may be part of a *Branhamella catarrhalis* strain or a bacterium that produces CD protein or produces a protein capable of generating antibodies in a host specifically reactive with CD protein.

In yet a further embodiment of the invention, there is provided a diagnostic kit for determining the presence of antibodies in a sample specifically reactive with CD protein, comprising:

(a) the CD protein as provided herein;

(b) means for contacting the CD protein with the sample to produce complexes comprising the CD protein and any said antibodies present in the sample; and (c) means for determining production of the complexes.

The invention also provides a diagnostic kit for detecting the presence of CD protein in a sample, comprising:

(a) an antibody specific for CD protein as provided herein;

(b) means for contacting the antibody with the sample to produce a complex comprising CD protein and CD-specific antibody; and (c) means for determining production of the complex.

In an additional aspect of the invention there is provided a method of providing an isolated and purified outer membrane protein CD of a bacterial strain that produces the CD protein, comprising the steps of:

(a) providing a cell mass of the bacterial strain;

(b) disrupting the cell mass to provide a cell lysate;

(c) fractionating the cell lysate to provide a first supernatant and a first pellet, the first supernatant comprising substantially a large proportion of soluble bacterial proteins;

(d) separating said first supernatant from said first pellet, (e) extracting the first pellet to remove substantially all soluble proteins and membrane proteins other than CD protein therefrom to provide a second supernatant and an extracted pellet containing CD protein;

(f) separating said second supernatant from said extracted pellet, (g) solubilizing the extracted pellet to provide a solubilized extract;

(h) fractionating the solubilized extract to provide a CD protein-containing supernatant and a discard pellet; and (i) separating the CD protein-containing supernatant from the discard pellet.

The bacterial strain producing CD protein may be a *Branhamella catarrhalis*. The cell lysate may be fractionated by centrifugation thereof and the solubilized extract may be fractionated by centrifugation thereof. The step of selectively extracting the first pellet may comprise at least one (including multiple) detergent extractions. The extracted pellet may be dispensed and solubilized with a buffered solution comprising a detergent and a solubilizing agent at a temperature and for a time to effect solubilization of the extracted pellet to provide the solubilized extract. The buffered solution may have a pH from about 7 to about 8.5 and may contain about 0.1 to about 2 wt % detergent, for example, Triton X-100, and from about 3 to about 8 molar urea as the solubilizing agent, such as about 4M. The solubilization may be effected at a temperature of about 40° to about 70° C. for about 10 to about 120 minutes.

The CD-containing supernatant usually is subsequently dialyzed to remove detergent and solubilizing agent to provide a further purified solution of CD protein in undenatured form.

In a further aspect of the invention there is provided a non-clumping strain of *Branhamella catarrhalis* having the identifying characteristics of *Branhamella catarrhalis* RH408 (ATCC 55637). Such non-clumping strain may be particularly advantageous for growth in large scale fermenters where clumping may be a problem. This non-clumping strain may be employed in a method of determining the anti-Branhamella anti-bacteriacidal activity of a antiserum, in a further aspect of the invention, which comprises:

effecting complement-mediated killing of a preselected number of cells of the non-clumping strain by the antiserum, and determining the proportion of the preselected number of cells killed by said antiserum as a measure of said anti-Branhamella anti-bacteriacidal activity.

Advantages of the present invention include:

a simple method for isolating, purified CD outer membrane protein of a bacterial strain that produces CD protein, including *Branhamella catarrhalis*;

an isolated and purified non-denatured outer membrane protein CD isolatable from a of Branhamella strain; and diagnostic kits and immunological reagents for specific identification of Branhamella and hosts infected thereby.

BRIEF DESCRIPTION OF THE FIGURES

The present invention will be further understood from the following description with reference to the Figures, in which.

GENERAL DESCRIPTION OF INVENTION

The present invention provides novel techniques which can be employed for preparing essentially pure CD outer membrane protein. Any bacterium that produces CD protein or produces a protein capable of generating antibodies that specifically recognize CD protein, a fragment or analog thereof may be conveniently used to provide the isolated and purified outer membrane protein CD as provided herein. The invention includes CD protein produced by recombinant means and analogs thereof which retain the immunogenic properties of the CD protein. The bacterium is generally a bacterial pathogen and typically is a strain of Branhamella, such as B. catarrhalis. Such strains are generally available from clinical sources and from bacterial culture collections. Appropriate strains of B. catarrhalis may include B. catarrhalis 4223 and B. catarrhalis RH408.

Figure 1:
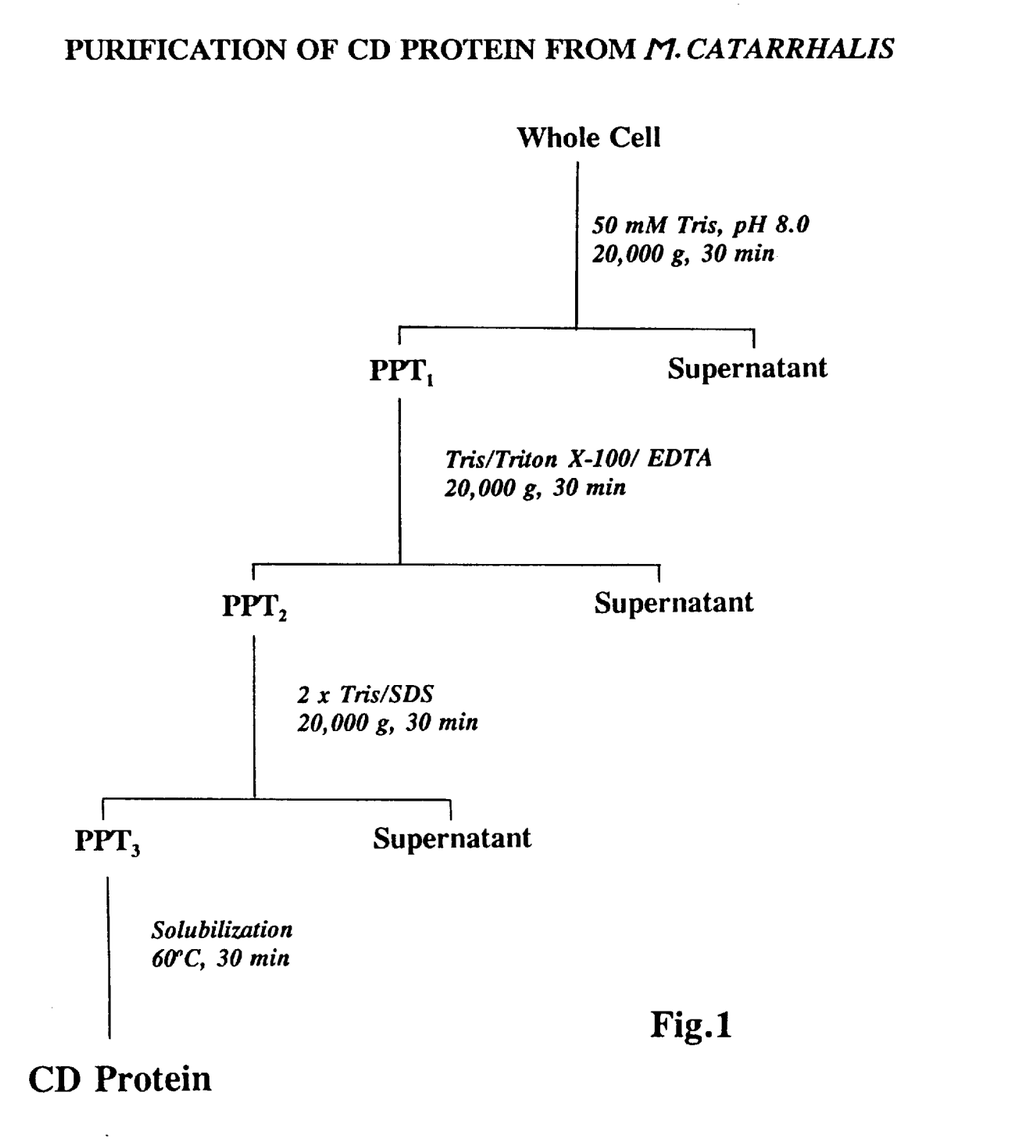
FIG. 1 is a flow diagram of a method for purifying CD protein from *Branhamella catarrhalis*, according to one embodiment of the invention.

Referring to FIG. 1, there is illustrated a flow diagram of a method for purifying CD protein from B. catarrhalis according to one embodiment of the invention. Whole cells are lysed under conventional buffered conditions to produce a cell lysate. The cell lysate is centrifuged to produce a supernatant containing about 95% of the soluble protein which is discarded and a pellet ($PPT_1$). This pellet is selectively detergent extracted to remove residual soluble proteins and membrane proteins other than the CD protein from the pellet ($PPT_1$) as well as other contaminants, including phospholipids and lipopolysaccharides. Such selective extraction may be effected in any convenient manner. One such procedure may involve multiple detergent extractions of the pellet. In particular, a first detergent extraction may be effected using Triton X-100 to remove substantially the residual soluble proteins followed by centrifugation to form a further pellet ($PPT_2$), with the supernatant again being discarded. Such Triton X-100 extraction may be effected using a solution of concentration about 0.2 to about 1 wt % Triton X-100 under buffer conditions, such as a pH about 7 to about 8.5, typically using Tris at pH 8.0.

Further detergent extraction of $PPT_2$ may be effected using sodium dodecylsulfate (SDS) or other convenient detergent, such as sodium deoxycholate, applied in one or more applications to remove substantially the outer membrane proteins other than CD protein and to provide removal of other contaminants, followed by centrifugation to a form a further pellet ($PPT_3$), with the supernatant again being discarded. Such further detergent extraction may be effected using a solution of concentration about 0.1 to about 1 wt % of detergent. Higher concentrations tend to cause some solubilization of CD protein and hence loss of yield and generally are avoided. Such detergent solution generally is used under buffered condition, such as about 7 to about 8.5, typically using Tris at pH 8.0.

The detergent extraction effected on the $PPT_1$ to product $PPT_3$ may be carried out over a convenient range of temperature, such as from about 4° to about 30° C. While the above-described selective extraction procedure involves detergent extraction with the different detergents, the selective extraction may be effected with a single detergent of suitable selective extraction capacity.

The solid phase ($PPT_3$) resulting from the selective detergent extraction of the cell lysate pellet contains CD protein and residual cellular debris and is substantially free from other bacterial proteins and contaminants. The CD protein then is solubilized from the solid phase and separated from the cellular debris, such as by centrifugation of the resulting solution. Such solubilization may be effected by first dispersing the solid phase using a detergent solution and then using a protein-solubilizing agent, such as urea, to solubilize the suspended CD protein, followed by centrifugation to remove suspended cellular debris.

The detergent solution used for dispersing the solid phase ($PPT_3$) may be any convenient detergent, such as Triton X-100, at a concentration of about 0.1 to about 2 wt %, under buffered conditions, such as about pH 7 to about 8.5. The amount of solubilizing agent used should be at least sufficient to solubilize substantially all the suspended CD protein. For example, when urea is used, a concentration of about 3 to about 8M may be used. The solubilization procedure is facilitated by the use of elevated temperature, such as about 40° to about 70° C., and may be effected for a time at least sufficient to effect substantially complete solubilization of CD protein, such as about 10 to about 120 minutes.

Following separation of the CD protein solution from the pellet of residual debris, the solubilizing agent is removed by any convenient procedure, such as by dialysis under conventional conditions, to provide a CD protein solution. By this procedure, there is provided in aqueous solution an isolated and purified non-denatured outer membrane CD protein. The aqueous CD protein solution may be provided in any convenient concentration consistent with the intended use of the material, generally about 100 to about 200 μg/mL. Further concentration of the solution may be effected by any convenient procedure.

Figure 2:
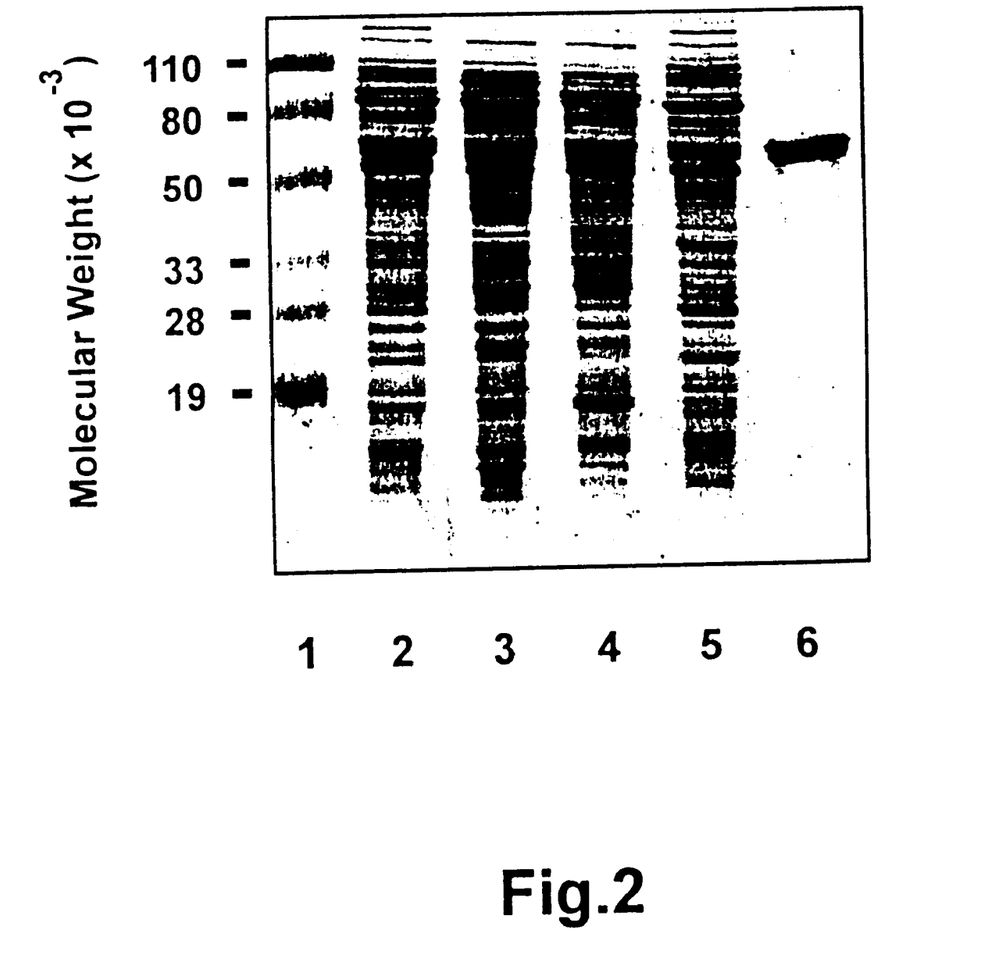
FIG. 2 shows an analysis of isolated and purified CD protein by SDS-PAGE.

Referring to FIG. 2, there is shown an analysis of the purity of CD protein by SDS-PAGE analysis, purified by the method described herein as typified by that schematically shown in FIG. 1. In FIG. 2, Lane 2 shows the B. catarrhalis cell lysate. Lane 3 shows the supernatant containing about 95% of the soluble protein obtained by treatment of the cell lysate with 50 mM Tris pH 8.0 and centrifugation. Lanes 4 and 5 show the supernatants obtained after one and two detergent extractions of the pellet obtained by treatment of the cell lysate with 50 mM Tris pH 8.0 and centrifugation respectively. Lane 6 shows the purified CD protein which has the known molecular weight of the protein. The method for purification of outer membrane CD protein as provided herein produces at least a 70% pure CD protein preparation. The illustrated preparation in Lane 6 in FIG. 2 is at least 95% pure, as determined by densitometry scanning.

Figure 3:
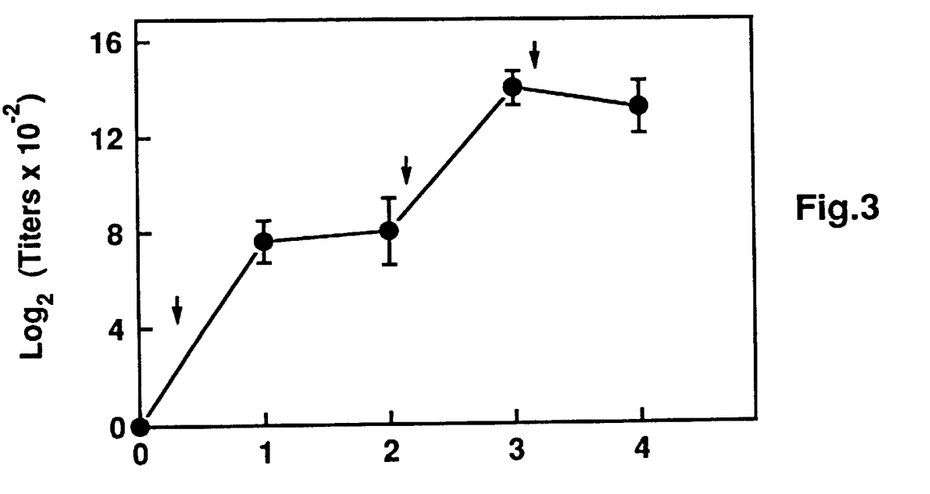
FIG. 3 illustrates the generation of CD-specific antibodies in mice by immunization with whole *B. catarrhalis;*
Figure 4:
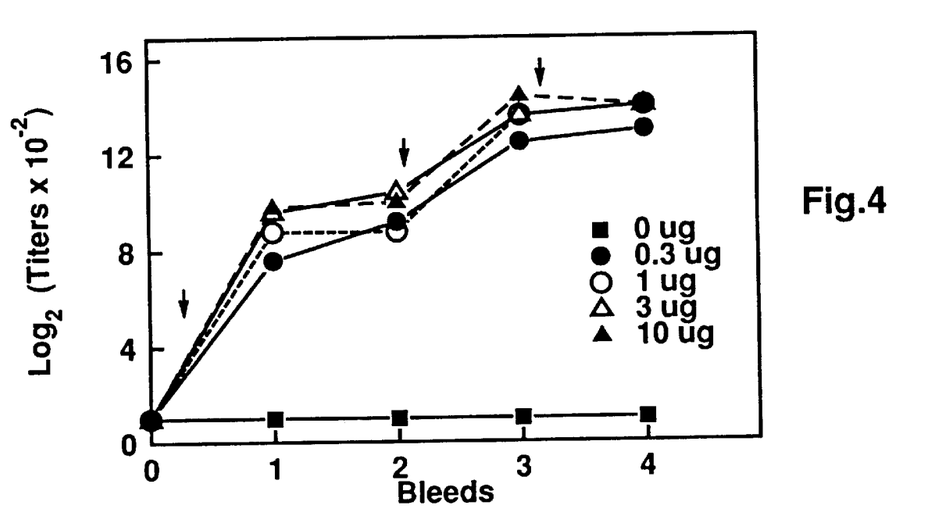
FIG. 4 illustrates the generation of CD-specific antibodies in mice by immunization with isolated and purified CD protein.

Referring to FIGS. 3 and 4, there is illustrated the immunogenicity of isolated and purified outer membrane protein CD of the present invention in mice. FIG. 3 illustrates the production of CD-specific antibodies in mice following immunization with whole B. catarrhalis cells. FIG. 4 illustrates the generation of specific antibodies following immunization with the purified CD protein of the invention. As may be seen from this data, the purified CD protein is highly immunogenic and of comparable immunogenicity to the CD protein in the bacterium.

Figure 5:
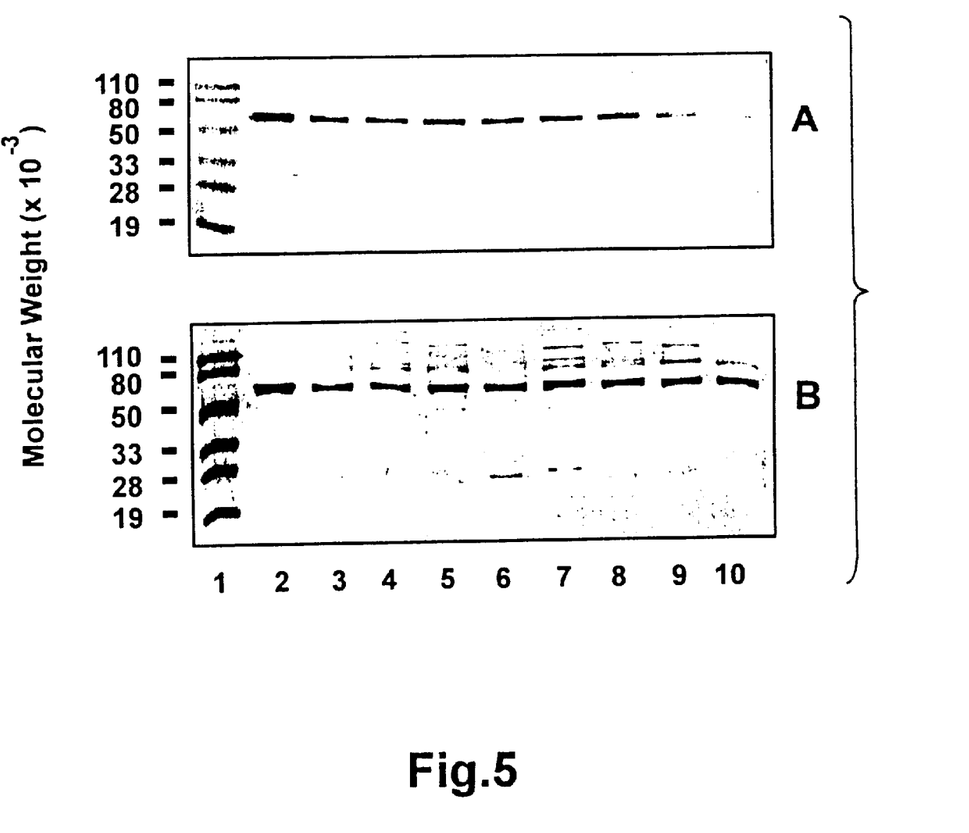
FIG. 5, comprising panels A and B, contains immunoblots showing the antigenic conservation of CD among a number of B. catarrhalis strains.

To be useful as a component of immunogenic compositions (including vaccines) and as an antigen in diagnostic embodiments, the CD protein purified as described herein should advantageously be capable of generating antibodies that recognize or neutralize a plurality of Branhamella catarrhalis strains. Referring to FIG. 5 (Panel A), there is illustrated an immunoblot showing the ability of mouse anti-CD antisera produced by immunizing mice with purified CD protein as provided herein to recognize CD protein from Branhamella catarrhalis isolated from a variety of sources. The B. catarrhalis strains tested were as follows:

| Lane | B. catarrhalis | Source |
|---|---|---|
| 2 | Purified CD | Present invention |
| 3 | 4223 | Middle ear fluid |
| 4 | 5191 | Middle ear fluid |
| 5 | 59 | Sputum |
| 6 | 25240 | ATCC 25240 |
| 7 | 135 | Middle ear fluid |
| 8 | 585 | Blood |
| 9 | 3 | Sputum |
| 10 | 8185 | Nasopharynx |

FIG. 5 (Panel B) also shows that immune sera obtained by immunizing mice with whole-inactivated B. catoarrhalis cells showed high reactivity with purified CD protein (lane 2) or the strains of B. catarrhalis (lanes 3 to 10). This indicates that the CD protein is a highly immunogenic protein in B. catarrhalis.

Figure 6:
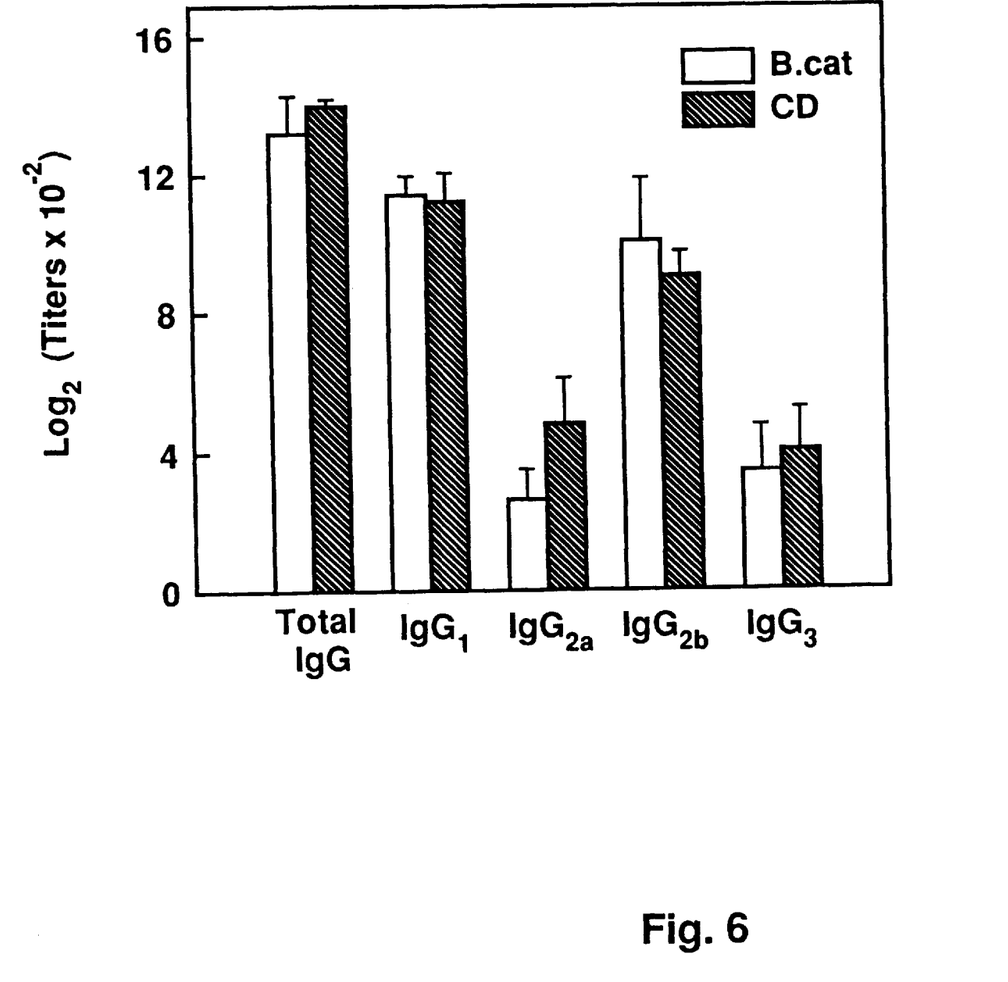
FIG. 6 shows a comparison of the IgG-subclass profile in mice produced by immunization either with whole B. catarrhalis or isolated and purified CD protein.

Referring to FIG. 6, there is shown a comparison of the anti-CD IgG subclass profile produced in mice by immunization either with whole inactivated B. catarrhalis cells or the isolated and purified CD protein provided herein. The most predominant responses were of the IgG, and $IgG_2$ isotypes. Furthermore, the IgG subclass profile produced by immunization with whole inactivated B. catarrhalis cells or purified CD protein were very similar, indicating the isolated and purified CD protein as described herein to be substantially in its native conformation.

Figure 7:
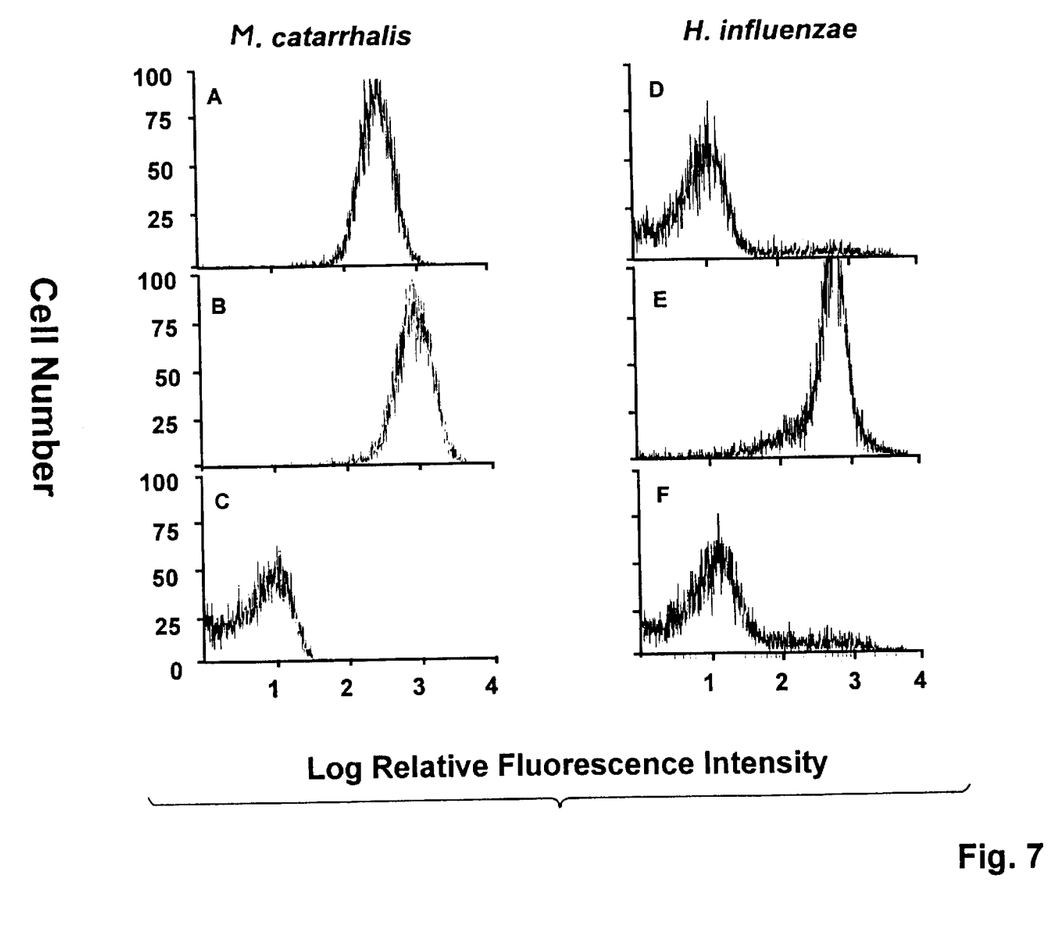
FIG. 7, comprising panels A to F shows the ability of mouse antisera produced by immunization either with whole B. catarrhalis or isolated and purified CD protein to bind to CD protein expressed on the surface of B. catarrhalis by flow cytometry.

Referring to FIG. 7, there is illustrated a flow cytometry analysis of anti-CD antisera binding to B. catarrhalis. Pooled mouse and anti-CD antisera produced by immunization with isolated and purified CD protein as described herein had nearly the same ability to bind to intact B. catarrhalis (Panel A) as that of anti-B. catarrhalis produced by immunization with whole B. catarrhalis cells (Panel B). Binding was specific to B. catarrhalis, since the same anti-CD antisera did not show significant binding to a bacterium that does not produce CD protein, H. influenzae (Panel D). In contrast, pooled mouse anti-H. influenzae antisera reacted strongly with H. influenzae (Panel E).

Panels C and F illustrate the substantial lack of binding of pre-immune sera to B. catarrhalis and H. influenzae respectively. This flow cytometry analysis indicates that anti-CD antibodies obtained by immunization with isolated and purified CD protein as provided herein recognize CD protein on the surface of intact B. catarrhalis and is evidence that the CD protein as provided herein is in substantially its native conformation.

Figure 8A:
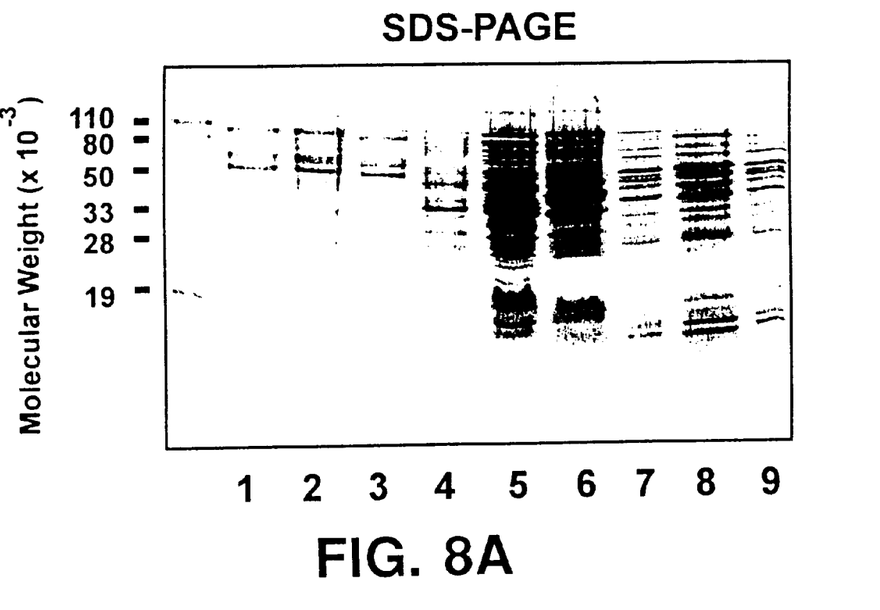
FIG. 8, comprising panels A and B, contains immunoblots to demonstrate the ability of mouse anti-CD antisera produced by immunization with isolated and purified CD protein to specifically distinguish between B. catarrhalis and other bacterial pathogens that cause otitis media.
Figure 8B:
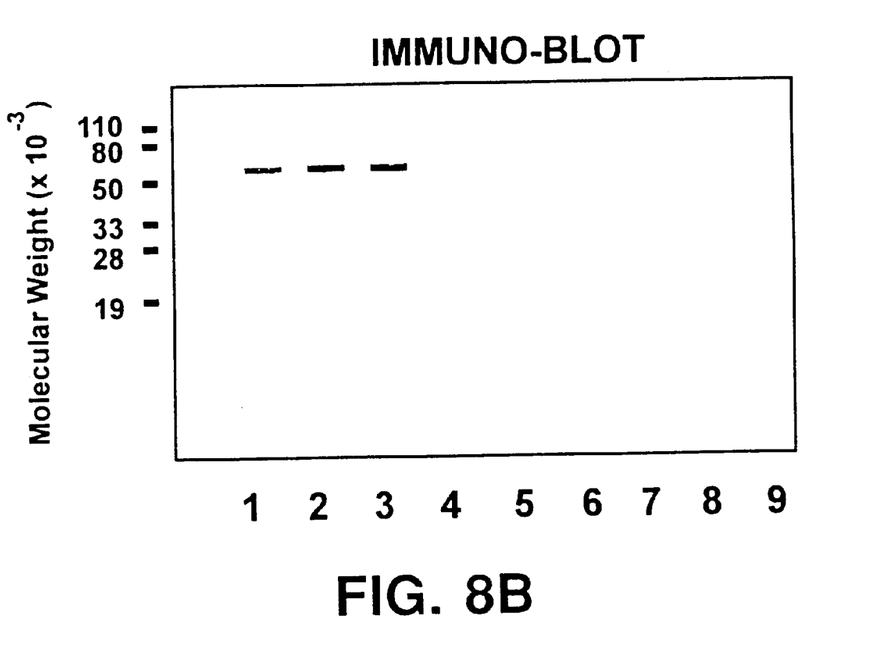

In one embodiment of the present invention, the isolated and purified CD protein as provided herein is useful for generating antibodies that can be used to specifically distinguish B. catarrhalis from other bacterial pathogens that cause otitis media. Thus referring to FIG. 8, there is illustrated an immunoblot showing the specific reactivity of mouse anti-CD antisera produced by immunizing mice with CD protein as provided herein. The bacteria analyzed were as follows:

| Lane | Bacterium | Source |
|---|---|---|
| 1 | B. catarrhalis 135 | Middle ear fluid |
| 2 | B. catarrhalis 5191 | Middle ear fluid |
| 3 | B. catarrhalis 4223 | Middle ear fluid |
| 4 | non-typable H. influenzae | Otitis media isolate |
| 5 | non-typable H. influenzae | Otitis media isolate |
| 6 | non-typable H. influenzae | Otitis media isolate |
| 7. | S. pneumoniae | ATCC 6304 |
| 8. | S. pneumoniae | ATCC 6306 |
| 9. | S. pneumoniae | ATCC 6314 |

The results shown in FIG. 8 clearly show the usefulness of CD-specific antisera as provided herein to distinguish between bacterial pathogens that produce diseases with similar clinical symptoms.

Results shown in Table 1 below illustrate the ability of either mouse or guinea pig anti-CD antisera produced by immunization with CD protein as provided herein, to lyse two different strains of B. catarrhalis. The results showed that both antisera produced by immunization with CD protein isolated from strain 4223 were bactericidal against a homologous non-clumping B. catarrhalis strain RH408 derived from strain 4223 and a heterologous non-clumping strain Q8 (a gift from Dr. M. G. Bergeron, Centre Hospitalier de l'Université Laval, St. Foy, Quebec). The bacteriacidal titers in guinea pig immune sera were very high (1:1,024). The bacteriacidal activities in mouse anti-CD antisera were around 1:128 against both strains, which were comparable to the titre obtained using anti-B. catarrhalis antisera produced by immunization with whole inactivated B. catarrhalis cells. The ability of the isolated and purified CD protein as provided herein to generate bacteriacidal antibodies is in vivo evidence of utility of the CD protein as a vaccine to protect against disease caused by B. catarrhalis or other bacteria that produce CD protein or produce a protein capable of generating antibodies that specifically recognize CD protein.

Thus, in accordance with another aspect of the present invention, there is provided a vaccine against Branhamella or other bacterial pathogens that produce CD protein or produce a protein capable of inducing antibodies that specifically recognize CD, comprising an immunogenically-effective amount of CD protein as provided herein and a physiologically-acceptable carrier therefor. The CD protein provided herein also may be used as a carrier protein for hapten, polysaccharides or peptides to make a conjugate vaccine against antigenic determinants unrelated to CD.

The CD protein provided herein is useful as a diagnostic reagent, as an antigen or for the generation of anti-CD antibodies, antigen for vaccination against the diseases caused by species of Branhamella and other bacterial pathogens that produce a protein capable of producing antibodies that specifically recognize CD and for detecting infection by Branhamella and other such bacteria.

In additional embodiments of the present invention, the CD protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial pathogens may include, for example, *Haemophilus influenzae, Streptococcus pneumoniae, Escherichia coli, Neisseria meningitides, Salmonella typhi, Streptococcus mutants, Cryptococcus neoformans,* Klebsiella, *Staphylococcus aureus* and *Pseudomonas aeruginosa*. Particular antigens which can be conjugated to CD protein and methods to achieve such conjugations are described in published PCT application WO 94/12641, assigned to the assignee hereof and the disclosure of which is hereby incorporated by reference thereto.

In another embodiment, the carrier function of CD protein may be used, for example, to induce immunity toward abnormal polysaccharides of tumor cells, or to produce anti-tumor antibodies that can be conjugated to chemotherapeutic or bioactive agents.

It is clearly apparent to one skilled in the art, that the various embodiments of the present invention have many applications in the fields of vaccination, diagnosis, treatment of, for example, Branhamella infections, and infections with other bacterial pathogens that produce proteins capable of producing antibodies that specifically recognize CD protein and the generation of immunological reagents. A further non-limiting discussion of such uses is further presented below.

1. Vaccine Preparation and Use

Immunogenic compositions, suitable to be used as vaccines, may be prepared from CD protein as disclosed herein. The vaccine elicits an immune response in a subject which produces antibodies, including anti-CD antibodies and antibodies that are opsonizing or bactericidal. Should the vaccinated subject be challenged by Branhamella or other bacteria that produce proteins capable of producing antibodies that specifically recognize CD protein, the antibodies bind to and inactivate the bacterium. Furthermore, opsonizing or bactericidal anti-CD antibodies may also provide protection by alternative mechanisms.

Immunogenic compositions including vaccines may be prepared as injectables, as liquid solutions or emulsions. The CD protein may be mixed with pharmaceutically acceptable excipients which are compatible with CD protein. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the CD protein. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the CD protein. Suitable regimes for initial administration and booster doses are also variable, but may include an initial administration followed by subsequent administrations. The dosage may also depend on the route of administration and will vary according to the size of the host.

The concentration of the CD antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diptheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 27) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 24), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller (ref. 25) describes a peptide with a sequence homologous to a foot-and-mouth disease viral protein coupled to an adjuvant tripalmityl-S-glyceryl-cysteinylserylserine, being a synthetic analogue of the N-terminal part of the lipoprotein from Gram negative bacteria. Furthermore, Deres et al. (ref. 26) reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-S-[2,3-bis(palmitylxy)-(2RS) -propyl- [R]-cysteine (TPC).

2. Immunoassays

The CD protein of the present invention is useful as an immunogen for the generation of anti-CD antibodies, as an antigen in immunoassays including enzyme-linked immunosorbent assays (ELISA), RIAs and other non-enzyme linked antibody binding assays or procedures known in the art for the detection of anti-bacterial, anti-Branhamella, and anti-CD antibodies. In ELISA assays, the CD protein is immobilized onto a selected surface, for example, a surface capable of binding proteins such as the wells of a polystyrene microtiter plate. After washing to remove incompletely adsorbed CD protein, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound CD protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example illustrates the growth of B. catarrhalis.

B. catarrhalis strain 4223 was inoculated into 20 mL of brain heart infusion (BHI) broth. The culture was incubated overnight with aeration at 37° C. For growth under iron-restricted conditions, one mL of the overnight-culture was inoculated into 20 mL of BHI broth containing 25 $\mu$M EDDA and the culture was grown at 37° C. for approximately 3 to 4 h. Cells grown to mid-log phase ($A_{578}>0.5$) were harvested by centrifugation at 10,000 ×g for 20 min.

The pellet was used for extraction of CD protein as described in Example 3.

Example 2

This Example illustrates the generation of a non-clumping strain (RH408) of *B. catarrhalis*.

*B. catarrhalis* strain 4223 was inoculated into several flasks containing 20 mL of BHI broth, and the cultures were incubated with shaking (170 rpm) overnight at 37° C. Five mL of each overnight culture were transferred to individual 1-mL tubes, and were left sitting undisturbed at room temperature for 3 to 8 h, to allow bacteria to sediment. One hundred μL of the cleared upper phase of each culture medium were used to inoculate 25 mL of BHI broth and cultures were incubated overnight at 37° C., as described above. This passaging was repeated six times, using 25 μL of cleared medium to inoculate 25 mL of BHI for each overnight culture. Non-clumping bacterial cultures were identified by measuring the $A_{578}$ at intervals over a 3 hr time period, in order to compare the sedimentation rates of the passaged strains to that of the original *B. catarrhalis* strain 4223 culture. Non-clumping mutants, including *B. catarrhalis* RH408, did not aggregate during the three hr time period. On BHI agar plates, strain RH408 had a colony morphology typical for all non-clumping strains. Strain RH408 is deposited under the terms of the Budapest Treaty at the American Type Culture Collection (ATCC) located at 10801 University Blvd., Manassas Va. 20110-2209, USA on Dec. 13, 1994 with Accession No. 55637.

Example 3

This Example illustrates the extraction and purification of CD protein.

CD protein was isolated from *B. catarrhalis* by the, procedure generally illustrated in FIG. 1. A cell pellet of *B. catarrhalis* from a 250 mL culture, prepared as described in Example 1, was resuspended in 40 mL of 50 mM Tris-HCl, pH 8.0, and disrupted by sonication (3×10 min, 70% duty circle). The extract was centrifuged at 20,000 ×g and the resultant supernatant, which contained more than 95% of the soluble proteins from *B. catarrhalis*, was discarded.

The residual pellet ($PPT_1$) was extracted first in 40 mL of 50 mM Tris, pH 8.0 containing 0.5% Triton X-100 and 10 mM EDTA and then twice in 40 mL of 50 mM Tris, pH 8.0 containing 0.5% SDS. These two extractions remove the residual soluble proteins as well as the majority of membrane proteins excluding CD protein.

The pellet obtained from the above extraction ($PPT_3$) was used as the starting material for CD purification. The pellet was resuspended in 50 mM Tris, pH 8.0, containing 0.5% Triton X-100, 10 mM EDTA. To the resulting suspension was added urea to a concentration of 6M, and then the suspension was heated at 60° C. for 30 min to solubilize the CD protein. After centrifugation at 20,000 g for 30 min., the resultant supernatant contained homogenous purified CD protein and was separated from the pellet. The purified CD protein solution was dialyzed against 50 mM Tris, pH 8.0 overnight to remove the urea and then further centrifuged at 20,000 ×g for 30 min. to remove any precipitated materials which may have come out of solution. The CD protein remained soluble under these conditions. The amount of CD in the final preparation was determined to be 100 μg/mL by the BCA protein assay and the purity of CD protein was assessed by SDS-PAGE analysis (see FIG. 2). The purity of the CD protein was about 95%. The SDS-PAGE analysis confirmed the CD protein producted had the known molecular weight for such protein (ref. 21). The identity of the purified CD protein was confirmed by amino acid sequence analysis of cyanogen bromide-cleavage fragments, in comparison to the published sequence (ref. 22). The purified CD protein was store at −20° C.

Example 4

This Example illustrates the immunization of mice and guinea pigs with purified CD protein.

Groups of five Balb/c mice were injected three times subcutaneously (s.c.) on days 1, 29 and 43 with either inactivated *B. catarrhalis* (about $10^5$ cells) or purified CD protein produced as described in Example 3 (0.3 μg to 10 μg) in the presence of $AlPO_4$ (1.5 mg per dose). Blood samples were taken on days 14, 28, 42 and 56 for analysing the anti-CD antibody titers by EIAs.

Groups of two guinea pigs (Charles River, Quebec) were immunized intramuscularly (i.m.) on day 1 with a 10 μg dose of purified CD protein emulsified in complete Freund's adjuvant (CFA). Animals were boosted on days 14 and 29 with the same dose of protein emulsified in incomplete Freund's adjuvant (IFA). Blood samples were taken on day 42 for analysing bacteriacidal activity of the antiserum.

Example 5

This Example illustrates the EIAs for determination of anti-C/D antibodies in mouse antisera.

EIAs were performed essentially as described by Panezutti et al. (ref. 23). Microtiter wells were coated with 1 μg of CD protein for 16 hours at room temperature. The plates were then blocked with 0.1% (w/v) bovine serum albumin in PBS. The mouse sera were serially diluted, added to the wells, then incubated for one hour at room temperature. Affinity-purified $F(ab')_2$ fragments of goat anti-mouse IgG (Fc specific) antibody conjugated to horseradish peroxidase were used as the second antibody. The reactions were developed using tetramethylbenzidine ($TMB/H_2O_2$) and absorbency was measured at 450 nm (using 540 nm as a reference wavelength) in a Flow Multiskan MCC microplate reader. The reactive titer of an antiserum was defined as the reciprocal of the dilution consistently showing a two-fold increase in absorbency over that obtained with the pre-immune serum sample.

Example 6

This Example illustrates the EIAs to determine the subclasses of anti-CD IgG in mouse sera.

Microtiter wells were coated with 1 μg of purified CD. The final bleeds of mouse serum samples from the immunogenicity study (as described in Example 4) were pooled and tested in EIAs. Rat anti-mouse $IgG_1$, $IgG_{2a}$, $IgG_{2b}$ antibodies conjugated to horseradish peroxidase and rabbit anti-mouse $IgG_3$ conjugated to horseradish peroxidase were used as reagents in EIAs. The working dilution of each conjugate was determined using purified antibody subclasses to avoid cross reactivity. The reactive titers were determined as described as one in Example 5.

Example 7

This Example illustrates the flow cytometry analysis.

*B. catarrhalis* strain RH408 was grown to approximately $2 \times 10^8$ cfu/ mL as described Example 1 and then a 100 μl aliquot mixed with 200 μl of antisera diluted 1/500 in PBS (4mM $Na_2HPO_4 \cdot 7H_2O$, 1.5 mM $KH_2PO_4$, 140 mM NaCl, 7 mM KCl, pH7.3) containing 1% BSA. The samples were then incubated at 4° C. for 30 min. *H. influenzae* strain 12 was also grown to 2×10$^8$ cfu/ mL, incubated with the same antisera and used as a negative control. Additional controls included incubation with the conjugates alone in the absence of any primary antiserum. After the primary incubation, the bacteria were washed twice with PBS/BSA (composition) and then mixed with 200 μl of diluted affinity purified Goat anti-mouse immunoglobulin-DTAF (Jackson ImmunoResearch Labs, Inc., Mississaga, Ontario). Bacteria were incubated with the conjugate for 30 min at 4° C., washed twice in PBS/BSA and resuspended in 1% paraformaldehyde.

The fluorescence of stained bacteria were assessed using a Coulter Elite flow cytometer. Ten thousand bacteria were evaluated in each analysis. An argon laser was employed and emission signals at 525 nm were collected. The level of antibody binding is expressed as the mean channel of fluorescence based on a log scale.

Example 8

This Example illustrates the bacteriacidal assay against *B. catarrhalis*.

Samples (25 μL) of antiserum, were heated to 56° C. for 30 min to remove complement activity and diluted 1:8 in veronal buffer (NaCl 8.0 g/L, NaHCO$_3$ 0.25 g/L, Na Barbiturate 0.30 g/L, Barbituric acid 0.45 g/L, MgCl$_2$.6H$_2$O 0.1 g/L, CaCl$_2$.2H$_2$O 0.05 g/L) containing 0.1% BSA (VBS), and then added to the first well of a 96-well Nunc microtiter plate. Twofold serial dilutions of antisera in VBS were placed in the remaining wells. Bacterial cells grown to an OD$_{578}$ >0.5 were diluted 1:200,000 in VBS and 25-μL portions of the bacterial suspension were added to each well. A guinea pig complement (Biowhittaker, Walkersville, Md.) was diluted 1:10 in VBS and 25 μL of the solution were added to each well to initiate reactions. The plates were incubated at 37° C. for 60 min, and 50 μL of each reaction mixture was then plated onto Mueller-Hinton agar plate containing 2.2% Mueller-Hinton broth and 1.5% agar. After incubation at 37° C. for 48 h, colonies were counted to determine the bacteriacidal titer (the reciprocal of the highest dilution of antiserum capable of killing greater than 50% of bacteria compared with controls containing pre-immune sera).

SUMMARY OF THE DISCLOSURE

In summary of this disclosure, the present invention provides an isolated and purified non-denatured outer membrane protein CD which is that of or corresponds to that isolated from a Branhamella strain and methods of isolating the same from bacterial strains. Modifications are possible within the scope of this invention.

TABLE 1

Bacterial activity of anti-CD antisera and anti-*B. catarrhalis* antisera against cida *B. catarrhalis*.

| Animal species | Antigen | *B. catarrhalis* strain | Bacteriacidal titer[1] | |
|---|---|---|---|---|
| | | | Pre-immune sera | Post-immune sera |
| Mouse[2] | CD | RH408 | <1:8 | 1:128 |
| Mouse | CD | Q8 | <1:8 | 1:128 |
| Mouse | Whole cell | RH408 | <1:8 | 1:512 |
| Mouse | Whole cell | Q8 | <1:8 | 1:512 |

TABLE 1-continued

Bacterial activity of anti-CD antisera and anti-*B. catarrhalis* antisera against cida *B. catarrhalis*.

| Animal species | Antigen | *B. catarrhalis* strain | Bacteriacidal titer[1] | |
|---|---|---|---|---|
| | | | Pre-immune sera | Post-immune sera |
| Guinea Pig[3] | CD | RH408 | <1:8 | 1:1,024 |
| Guinea Pig | CD | Q8 | <1:8 | 1:1,024 |

[1]Bacteriacidal titers are expressed as the highest dilution of antisera capable of killing 50% of cells compared with the control.
[2]Groups of five Balb/c mice were injected three times subcutaneously (s.c.) on days 1, 29 and 43 with either inactivated *B. catarrhalis* strain 4223 or 3 μg of purified CD in the presence of AlPO$_4$. Blood samples were taken on day 54 for analysing bacteriacidal activity.
[3]Groups of two guinea pigs (Charles River, Quebec) were immunized intramuscularly (i.m.) on day 1 with a 10 μg dose of purified CD protein emulsified in complete Freund's adjuvant (CFA). Animals were boosted on days 14 and 29 with the same dose of protein emulsified in incomplete Freund's adjuvant (IFA). Blood samples were taken on day 42 for analysing bacteriacidal activity.

References

1. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis*: biology and therapy. Rev. Infect. Dis. 9:16–27.
2. Chapman, A. J., D. M. Musher, S. Jonsson, J. E. Clarridge, and R. J. Wallace. 1985. Development of bactericidal antibody during *Branhamella catarrhalis* infection. J. Infect. Dis. 151:878–882.
3. Hager, H., A. Verghese, S. Alvarez, and S. L. Berk. 1987. *Branhamella catarrhalis* respiratory infections. Rev. Infect. Dis. 9:1140–1149.
4. McLeod, D. T., F. Ahmad, M. J. Croughan, and M. A. Calder. 1986. Bronchopulmonary infection due to *B. catarrhalis*. Clinical features and therapeutic response. Drugs 31(Suppl.3):109–112.
5. Nicotra, B., M. Rivera, J. I. Luman, and R. J. Wallace. 1986. *Branhamella catarrhalis* as a lower respiratory tract pathogen in patients with chronic lung disease. Arch.Intern.Med. 146:890–893.
6. Ninane, G., J. Joly, and M. Kraytman. 1978. Bronchopulmonary infection due to *Branhamella catarrhalis* 11 cases assessed by transtracheal puncture. Br.Med.Jr. 1:276–278.
7. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am.Rev. Respir. Dis. 123:553–555.
8. West, M., S. L. Berk, and J. K. Smith. 1982. *Branhamella catarrhalis* pneumonia. South.Med. J. 75:1021–1023.
9. Brorson, J-E., A. Axelsson, and S. E. Holm. 1976. Studies on *Branhamella catarrhalis* (*Neisseria catarrhalis*) with special reference to maxillary sinusitis. Scan. J. Infect. Dis. 8:151–155.
10. Evans, F. O., Jr., J. B. Sydnor, W. E. C. Moore, G. R. Moore, J. L. Manwaring, A. H. Brill, R. T. Jackson, S. Hanna, J. S. Skaar, L. V. Holdeman, G. S. Fitz-Hugh, M. A. Sande, and J. M. Gwaltney, Jr. 1975. Sinusitis of the maxillary antrum. N.Engl.J.Med. 293:735–739.
11. Tinkelman, D. G., and H. J. Silk. 1989. Clinical and bacteriologic features of chronic sinusitis in children. Am.J.Dis.Child. 143:938–942.
12. Wald, E. R., C. Byers, N. Guerra, M. Casselbrant, and D. Beste. 1989. Subacute sinusitis in children. J.Pediatr. 115:28–32.

13. Wald, E. R., G. J. Milmoe, A. Bowen, J. Ledesma-Medina, N. Salamon, and C. D.Bluestone. 1981. Acute maxillary sinusitis in children. N.Engl.J.Med. 304:749–754.
14. Christensen, J. J., and B. Bruun. 1985. Bacteremia caused by a beta-lactamase producing strain of *Branhamella catarrhalis*. Acta.Pathol. Microbiol. Immunol. Scand. Sect.B 93:273–275.
15. Craig, D. B., and P. A. Wehrle. 1983. *Branhamella catarrhalis* septic arthritis. J. Rheumatol. 10:985–986.
16. Gray, L. D., R. E. Van Scoy, J. P. Anhalt, and P. K. W. Yu. 1989. Wound infection caused by *Branhamella catarrhalis*. J.Clin.Microbiol. 27:818–820.
17. Guthrie, R., K. Bakenhaster, R. Nelson, and R. Woskobnick. 1988. *Branhamella catarrhalis* sepsis: a case report and review of the literature. J.Infect.Dis. 158:907–908.
18. Hiroshi, S., E. J. Anaissie, N. Khardori, and G. P. Bodey. 1988. *Branhamella catarrhalis* septicemia in patients with leukemia. Cancer 61:2315–2317.
19. O'Neill, J. H., and P. W. Mathieson. 1987. Meningitis due to *Branhamella catarrhalis* . Aust. N.Z. J. Med. 17:241–242.
20. Murphy, T. F. 1989. The surface of *Branhamella catarrhalis*: a systematic approach to the surface antigens of an emerging pathogen. Pediatr. Infect. Dis. J. 8:S75–S77.
21. Sarwar, J. Campagnari, A. A., Kirkham, C., and Murphy, T. F. 1992, Characterization of an antigenically conserved heat-modifiable major outer membrane protein of *Branhamella catarrhalis*. 1992. Infect.Immun. 60:804–809.
22. Murphy, T. F., C. Kirkham, and A. J. Lesse. 1993. The major heat-modifiable outer membrane protein CD is highly conserved among strains of *Branhamella catarrhalis*. Mol. Microbiol. 10(1):87–97.
23. Panezutti H., O. James, E. J. Hanson, Y. Choi, R. E. Harkness, M. H. Klein and P. Chong, 1993. Identification of surface-exposed B-cell epitopes recognized by *Haemophilus influenzae* type b P1 specific monoclonal antibodies. Infec. Immun. 61: 1867–1872.
24. Nixon-George et al. (1990), J. Immunology 144:4798–4802.
25. Wiesmuller (1989), Vaccine 8:29–33.
26. Deres et al. (1989), Nature 342:561.
27. Lockhoff, O. Glycolipids as Immmunomodulators: Synthesis and Properties. 1991. Chem. Int. Ed. Engl. 30:1611–1620.

What we claim is:

1. A method of producing an isolated and purified outer membrane protein CD of a Branhamella strain, comprising the steps of:

(a) providing a cell mass of the Branhamella strain;

(b) disrupting the cell mass to provide a cell lysate;

(c) fractionating the cell lysate to provide a first supernatant and a first pellet, the first supernatant comprising a large proportion of soluble bacterial proteins;

(d) separating said first supernatant from said first pellet;

(e) extracting the first pellet to remove soluble proteins and membrane proteins other than CD protein therefrom to provide a second supernatant and an extracted pellet containing CD protein;

(f) separating said second supernatant from said extracted pellet;

(g) solubilizing the extracted pellet to provide a solubilized extract;

(h) fractionating the solubilized extract to provide a CD protein-containing superntant and a discard pellet; and (i) recovering the separated CD-containing supernatant.

2. The method of claim 1 wherein said Branhamella strain is *Branhamella catarrhalis*.

3. The method of claim 1 wherein said cell lysate is fractionated by centrifugation and said solubilized extract is fractionated by centrifugation.

4. The method of claim 3 wherein said step of extracting the first pellet comprises at least one detergent extraction.

5. The method of claim 4 wherein said step of extracting the first pellet comprises multiple detergent extractions.

6. The method of claim 4 wherein the extracted pellet is dispersed and solubilized with a buffered solution comprising a detergent and a solubilizing agent at a temperature and for a time to effect solubilization of the extracted pellet to provide the solubilized extract.

7. The method of claim 6 wherein said buffered solution has a pH from about 7 to about 8.5 and contains about 0.1 to about 2 wt % detergent and from about 3 to about 8M urea as said solubilizing agent.

8. The method of claim 7 wherein said detergent is Triton X-100.

9. The method of claim 7 wherein said solubilization is effected at a temperature of about 40° to about 70° C. for about 10 to about 120 minutes.

10. The method of claim 6 including subsequently dialyzing the CD-containing supernatant to remove said detergent and solubilizing agent to provide a further purified solution of CD protein in undenatured form.

* * * * *